(12) United States Patent
Kasai et al.

(10) Patent No.: US 7,560,695 B2
(45) Date of Patent: Jul. 14, 2009

(54) DETECTING APPARATUS, AND DETECTING METHOD

(75) Inventors: Shintaro Kasai, Tokyo (JP); Toshihiko Ouchi, Sagamihara (JP); Takeaki Itsuji, Hiratsuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/727,673

(22) Filed: Mar. 28, 2007

(65) Prior Publication Data

US 2007/0235718 A1 Oct. 11, 2007

(30) Foreign Application Priority Data

Apr. 11, 2006 (JP) ............................. 2006-108563
Feb. 2, 2007 (JP) ............................. 2007-023610

(51) Int. Cl.
*G01J 5/20* (2006.01)
(52) U.S. Cl. .................................................. 250/338.4
(58) Field of Classification Search .... 250/338.1–338.4
See application file for complete search history.

(56) References Cited

U.S. PATENT DOCUMENTS

| | | | |
|---|---|---|---|
| 5,032,975 A | 7/1991 | Yamamoto et al. |
| 5,586,131 A | 12/1996 | Ono et al. |
| 5,659,560 A | 8/1997 | Ouchi et al. |
| 5,699,373 A | 12/1997 | Uchida et al. |
| 5,764,670 A | 6/1998 | Ouchi |
| 6,448,553 B1 | 9/2002 | Itsuji et al. |
| 6,835,925 B2 | 12/2004 | Itsuji et al. |
| 6,854,901 B1 | 2/2005 | Ouchi |
| 7,062,116 B2 | 6/2006 | Ouchi |
| 7,248,995 B2 | 7/2007 | Itsuji et al. |
| 2006/0039431 A1 | 2/2006 | Sekiguchi et al. |
| 2006/0061510 A1 | 3/2006 | Itsuji |
| 2006/0085160 A1 | 4/2006 | Ouchi |
| 2006/0188398 A1 | 8/2006 | Yano et al. |
| 2006/0197021 A1 | 9/2006 | Ouchi |
| 2006/0214176 A1 | 9/2006 | Ouchi et al. |

(Continued)

FOREIGN PATENT DOCUMENTS

JP 04326201 A * 11/1992

OTHER PUBLICATIONS

J. Zhang and D. Grischkowsky, "Terahertz time-domain spectroscopy of submonolayer water adsorption in hydrophilic silica aerogel", Optics Letters, vol. 29, pp. 1031-1033, May 1, 2004.*

(Continued)

*Primary Examiner*—David P Porta
*Assistant Examiner*—Kiho Kim
(74) *Attorney, Agent, or Firm*—Fitzpatrick, Cella, Harper & Scinto

(57) ABSTRACT

A detecting apparatus for detecting information of a liquid object or sample includes a transmission path, a THz wave supplying unit, a THz wave detecting unit, and an infiltrative holding member for infiltration and holding of a liquid object. The supplying unit supplies an electromagnetic wave in a frequency range between 30 GHz and 30 THz to the transmission path. The detecting unit detects the THz wave transmitted through the transmission path. The infiltrative holding member is set at a location containing at least a portion in which an electric field distribution of the THz wave propagating along the transmission path extends.

7 Claims, 10 Drawing Sheets

U.S. PATENT DOCUMENTS

| | | | |
|---|---|---|---|
| 2006/0226348 A1* | 10/2006 | Abreu et al. | 250/227.11 |
| 2006/0227340 A1 | 10/2006 | Shioda et al. | |
| 2006/0244629 A1 | 11/2006 | Miyazaki et al. | |
| 2007/0030115 A1 | 2/2007 | Itsuji et al. | |
| 2007/0195921 A1 | 8/2007 | Ouchi | |
| 2007/0215808 A1 | 9/2007 | Sekiguchi et al. | |
| 2007/0229094 A1 | 10/2007 | Kasai et al. | |
| 2007/0252604 A1 | 11/2007 | Ouchi et al. | |
| 2008/0048792 A1 | 2/2008 | Ouchi et al. | |

OTHER PUBLICATIONS

J. Zhang and D. Grischkowsky, "Waveguide Terahertz time-domain spectroscopy of nanometer water layers", Optics Letters, vol. 29, pp. 1617-1619, Jul. 15, 2004.*

R. Mandis and D. Grischkowsky, "THz interconnect with low-loss and low-group velocity dispersion", IEEE Microwave and Wireless Components Letters, vol. 11, Nov. 2001, pp. 444-446.*

K. Wang and D. Mittleman, "Metal wire waveguides for broadband terahertz pulses", Lasers and Electro-Optics Society (LEOS 2004), Nov. 7-11, 2004, vol. 1, pp. 372-373.*

Woodward et al., "Terahertz pulse imaging of ex vivo Basal Cell Carcinoma,", 2003, the Society for Invetigative Dermotalogy pp. 72-78.*

U.S. Appl. No. 11/632,958, International Filing Date: Aug. 10, 2006, Applicant(s): Toshihiko Ouchi.

U.S. Appl. No. 10/587,262, International Filing Date: Mar. 22, 2006, Applicant(s): Takeaki Itsuji.

U.S. Appl. No. 10/587,261, International Filing Date: Mar. 27, 2006, Applicant(s): Sekiguchi, et al.

M. Nagel, et al., "Integrated THz technology for label-free genetic diagnostics", Applied Physics Letters, vol. 80, No. 1, 2002, pp. 154-156.

* cited by examiner

FIG.1A
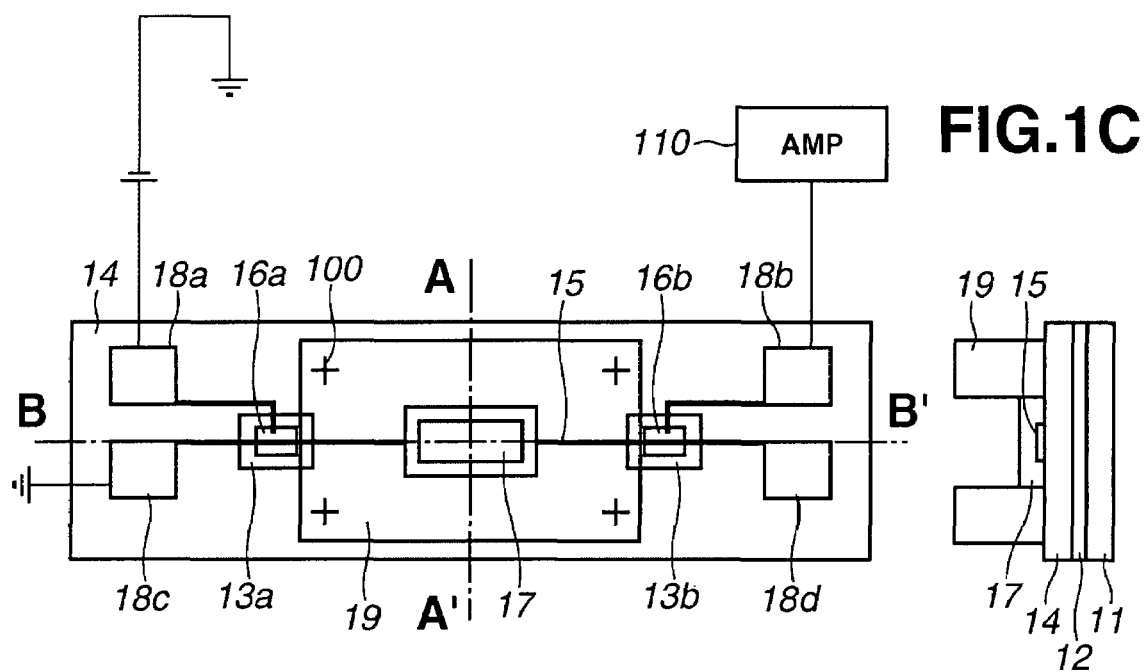
FIG.1C
FIG.1B
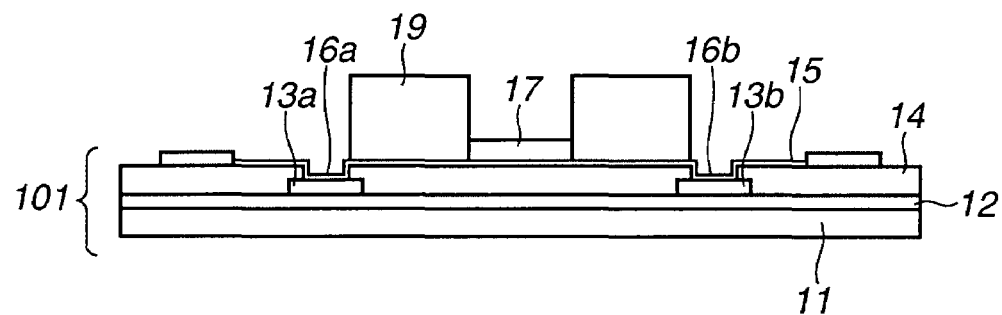

FIG.4A
FIG.4C
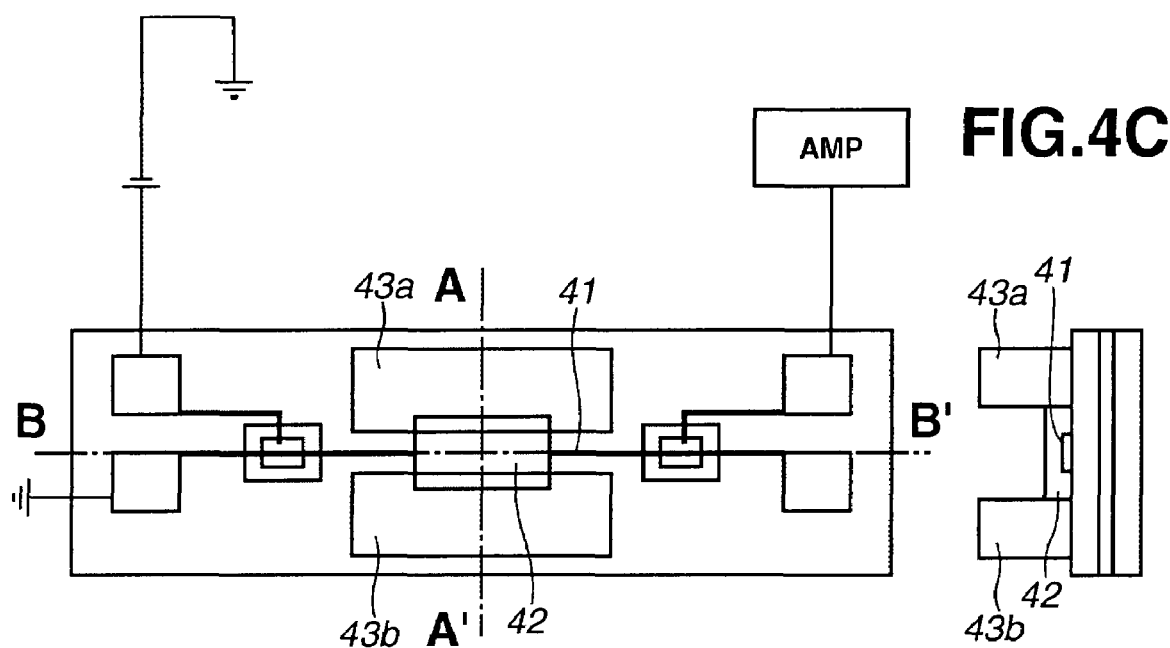
FIG.4B
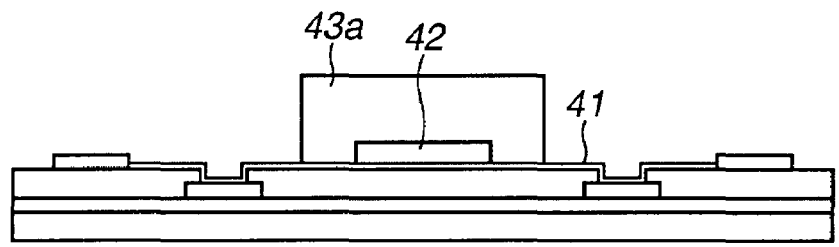

FIG.5A
FIG.5C
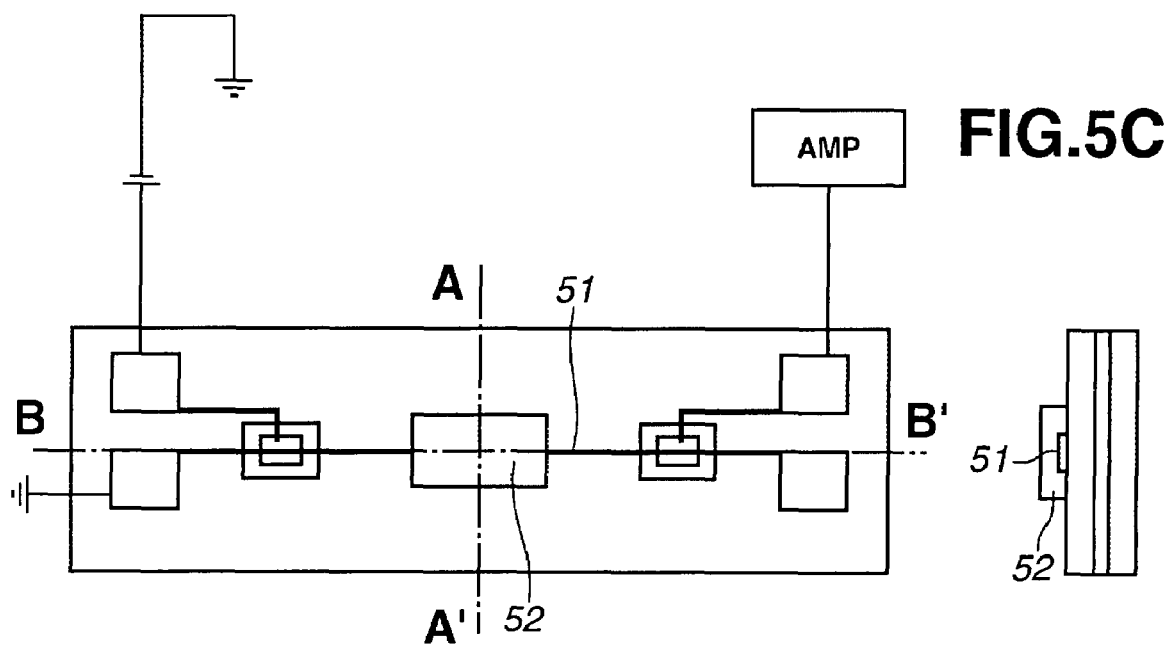
FIG.5B
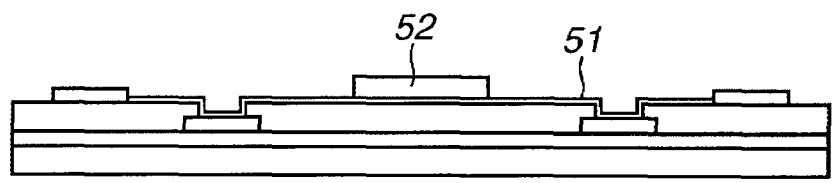

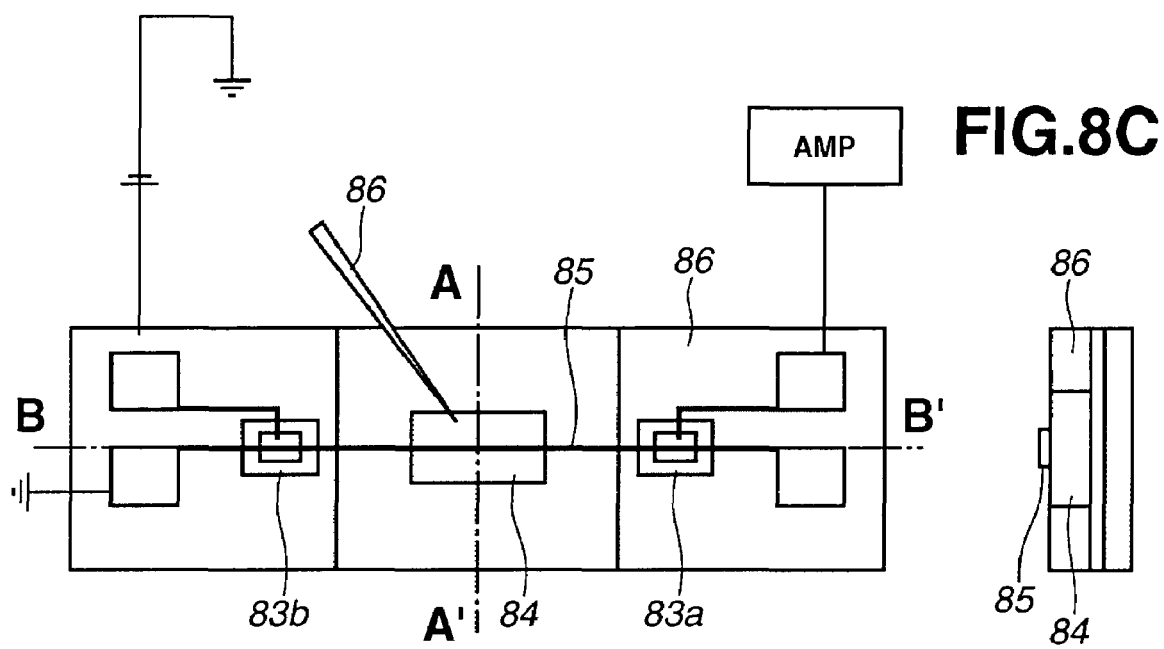
FIG.8A
FIG.8C
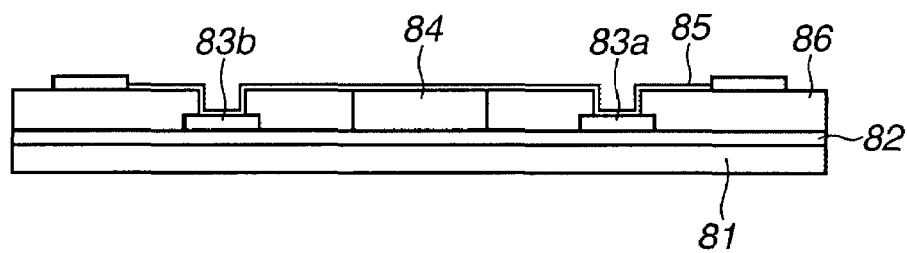
FIG.8B

DETECTING APPARATUS, AND DETECTING METHOD

BACKGROUND OF THE INVENTION

1. Field of the Invention

The present invention relates to a detecting apparatus and method for detecting information, such as characteristics, identification, concentration, and presence or absence, of a liquid object or sample, by using an electromagnetic wave. Particularly, the present invention relates to a detecting apparatus and method using an electromagnetic wave at a frequency or frequencies including at least a portion of a frequency range from 30 GHz to 30 THz. The electromagnetic wave including at least a component in the above frequency range is called a THz wave in this specification.

2. Description of Related Art

In recent years, techniques using a THz wave have been energetically researched and developed. In particular, photon energy of a THz wave is approximately equal to energies of molecular skeleton vibration and intermolecular action of material, and hence, techniques using a THz wave are employed in analysis of material that uses spectra, etc. obtained by the spectroscopic method.

In the above situation, "APPLIED PHYSICS LETTERS/Vol. 80, No. 1, 2002, p. 154" discloses a proposal in which a THz-wave transmission path is formed on a substrate, DNA water solution is dripped and dried on the transmission path, and analysis of the DNA is carried out by detecting a change in a THz-wave transmission property of the transmission path. The proposal uses the fact that a dielectric constant of single-stranded DNA for the THz wave differs from that of double-stranded DNA, and shows that single-stranded DNA and double-stranded DNA can be separately identified based on a difference in the THz-wave transmission property of the transmission path.

As stated above, when optical characteristics of material, such as an absorption coefficient, complex refractive index, and the like, are obtained by detecting a change in a transmission condition of a THz wave used, analysis, detection, identification, etc. of the material can be conducted. In the method of the above reference, however, no means is used for dripping a liquid sample onto the transmission path in an improved controllability, and accordingly it is typically not easy to accurately drip the sample on the transmission path. The dripped liquid sample is likely to flow and spread, so a location of the dripped sample on the transmission path and an interaction area between the THz wave and the sample are not easy to appropriately regulate.

SUMMARY OF THE INVENTION

It is therefore an object of the present invention to provide a detecting apparatus and method for detecting information of a liquid object or sample using THz wave.

According to one aspect of the present invention, there is provided a detecting apparatus for detecting information of a liquid object or sample, which includes a transmission path, a THz wave supplying unit, a THz wave detecting unit, and an infiltrative holding member for infiltration and holding of a liquid sample. The supplying unit supplies electromagnetic radiation in a frequency range between 30 GHz and 30 THz, or THz wave, to the transmission path. The detecting unit detects the THz wave transmitted through the transmission path. The infiltrative holding member is set at a location containing at least a portion in which an electric field distribution of the THz wave propagating along the transmission path extends.

According to another aspect of the present invention, there is provided a detecting method for detecting information of a liquid object or sample, which includes a step of preparing an apparatus including a transmission path, a THz wave supplying unit, and a THz wave detecting unit, and a second of setting an infiltrative holding member for infiltration and holding of a liquid sample at a location containing at least a portion in which an electric field distribution of THz wave propagating along the transmission path extends. The supplying unit supplies electromagnetic wave in a frequency range between 30 GHz and 30 THz, or THz wave, to the transmission path. The detecting unit detects the THz wave transmitted through the transmission path. In the detecting method, the THz wave is supplied to the transmission path under a condition in which the liquid sample is infiltrated and held in the infiltrative holding member, and the THz wave transmitted through the transmission path is detected to detect information of the liquid sample.

According to the present invention, the infiltrative holding member for infiltration and holding of a liquid object or sample is used, so the location of the dripped liquid object or sample on the transmission path and the interaction area between the THz wave and the liquid object or sample can be accurately and precisely regulated.

The features of the present invention will be more readily understood in connection with the following detailed description of the embodiments and examples of the invention in connection with the drawings.

BRIEF DESCRIPTION OF THE DRAWINGS

FIG. 1A is a plan view illustrating a first embodiment and example of a detecting apparatus and method according to the present invention, which uses an infiltrative holding member for infiltration and holding of a liquid sample.

FIG. 1B is a cross-sectional view taken along line B-B' of FIG. 1A.

FIG. 1C is a cross-sectional view taken along line A-A' of FIG. 1A.

FIG. 4A is a plan view illustrating a second embodiment of a detecting apparatus and method according to the present invention, in which two sides of an infiltrative holding member (a porous material) for infiltration and holding of a liquid sample are set by non-infiltrative members (resin plates).

FIG. 4B is a cross-sectional view taken along line B-B' of FIG. 4A.

FIG. 4C is a cross-sectional view taken along line A-A' of FIG. 4A.

FIG. 5A is a plan view illustrating a third embodiment of a detecting apparatus and method according to the present invention, in which an infiltrative holding member (a porous material) for infiltration and holding of a liquid sample is set by bonding.

FIG. 5B is a cross-sectional view taken along line B-B' of FIG. 5A.

FIG. 5C is a cross-sectional view taken along line A-A' of FIG. 5A.

FIG. 8A is a plan view illustrating a sixth embodiment of a detecting apparatus and method according to the present invention, in which a dielectric layer includes an infiltrative holding member (a porous material) for infiltration and holding of a liquid sample.

FIG. 8B is a cross-sectional view taken along line A-B' of FIG. 8A.

FIG. 8C is a cross-sectional view taken along line A-A' of FIG. 8A.

DESCRIPTION OF THE EMBODIMENTS

Figure 2:
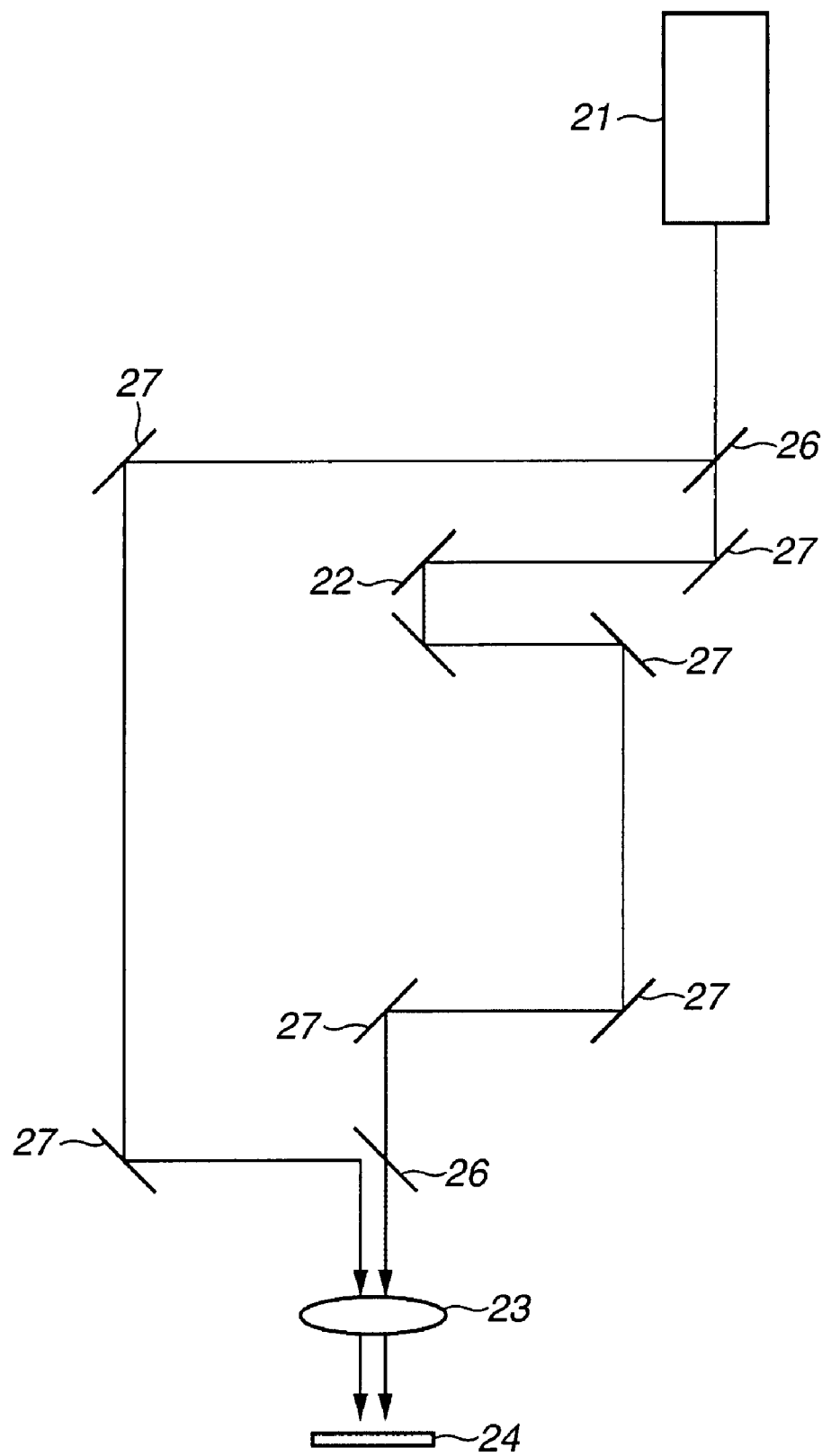
FIG. 2 is a view illustrating an optical system for supplying laser light to a transmission path of the detecting apparatus of the present invention.

Embodiments and examples of a detecting apparatus and method for detecting information of a liquid object of the present invention will hereinafter be described with reference to the drawings.

A typical embodiment of apparatus for detecting information of a liquid object or sample includes a transmission path for transmitting THz wave therethrough, a THz-wave supplying unit for supplying THz wave to the transmission path through a coupling portion, and a THz-wave detecting unit for detecting the THz wave received from the transmission path via a coupling portion. Further, there is provided an infiltrative holding member for infiltration and holding of a liquid sample by capillary force, surface tension, etc. around the transmission path, or in a portion of a dielectric layer forming the transmission path.

The infiltrative holding member is set at a location containing at least a portion in which an electric field distribution of the THz wave propagating along the transmission path extends. In the above construction, the detecting unit can obtain information of a change in a transmission condition of the THz wave transmitted through the transmission path caused by constituents of the liquid sample, its presence or absence, etc. Thus, information of the liquid sample can be acquired.

The infiltrative holding member allows the liquid sample supplied by dripping or the like to be uniformly infiltrated therein by capillary force, etc. and held therein. The infiltrative holding member prevents the liquid sample from flowing out. Further, even in the event that the liquid sample dries and its solute precipitates in the infiltrative holding member, the solute is uniformly held in the infiltrative holding member. Here, the wording of "uniformly" means that the sample gives a substantially uniform action to the THz wave used. In other words, when observing the sample at a positional resolution of about a wavelength of the THz wave used, the sample uniformly behaves for the THz wave.

Accordingly, when the infiltrative holding member is accurately set, the interaction area between the THz wave propagating along the transmission path and the sample held in the infiltrative holding member is virtually always established in an appropriate manner. This is also assured by the fact that the liquid sample dripped on any position of the infiltrative holding member infiltrates into the entirety thereof virtually without fail. Accordingly, even quantitative detection of measuring the concentration of the sample, and the like can be accurately achieved.

A constituent material of the infiltrative holding member is preferably a material having a high transmissivity for the THz wave used. The structure of the infiltrative holding member can be porous, fibrous, needle-like, or the like. The dimension (i.e., diameter of porosity, thickness of fiber or distance between fibers, or thickness of needle or distance between needles) of a fine structure thereof is desirably smaller enough than the wavelength of the THz wave used such that it does not scatter the radiation.

The length of a longitudinal side of the infiltrative holding member is preferably less than the length of the transmission path. The reason therefor is that the interaction area between the liquid sample and the THz wave propagating along the transmission path is regulated by the size of the infiltrative holding member, since the liquid sample infiltrates almost into the entirety of the infiltrative holding member when the sample is dripped on the infiltrative holding member. Further, the electric field distribution of the propagating THz wave is exceedingly weak outside the transmission path, and hence this does not contribute to the detection. However, even an infiltrative holding member with a longitudinal side longer than the transmission path can be used when a mechanism for preventing infiltration of the liquid sample beyond an area of the transmission path is formed. This is, for example, a mechanism for preventing infiltration beyond a desired region by pressing and crushing a portion of the infiltrative holding member with a frame member made of a non-infiltrative material.

As a method for infiltrating and holding a liquid sample in the infiltrative holding member, injecting means, such as a micro-injector and a pipette capable of dripping a minute drop of liquid, can be used.

When the amount of a liquid sample supplied onto the infiltrative holding member exceeds its infiltrative holding ability, there is a possibility that the liquid sample comes out from the infiltrative holding member. In such a case, it is preferable to dispose a non-infiltrative member incapable of infiltration of the liquid sample (e.g., a solid resin) adjacent to a part or the entirety of the infiltrative holding member. Thereby, the liquid sample can be assuredly prevented from coming out from the infiltrative holding member, and the interaction area between the liquid sample and the THz wave can be accurately regulated.

When the amount of dripped liquid sample exceeds the volume of a space formed by the non-infiltrative member, the volume of the liquid sample can be maintained at a predetermined value by wiping and removing overflowing liquid sample.

The non-infiltrative member can be disposed adjacent to at least a portion (e.g., two sides, or four sides) of the infiltrative holding member to hold it at a predetermined location near the transmission path. In the case of two sides, for example, the non-infiltrative member is disposed to adjoin two sides or surfaces of the infiltrative holding member extending along the transmission path. In the case of four sides, the non-infiltrative member is disposed to adjoin two sides or surfaces of the infiltrative holding member extending along the transmission path, and two sides or surfaces thereof extending in a direction traversing the transmission path.

When the non-infiltrative member is disposed adjacent to a portion or the entirety of the infiltrative holding member, a spacing below a wavelength of the THz wave used can be formed between the infiltrative holding member and the non-infiltrative member. The liquid sample can be supplied to the infiltrative holding member using the spacing as a guiding flow path. In another configuration, the infiltrative holding member can be brought into close contact with the non-infiltrative member.

When the non-infiltrative member is used, there is a case where an optical constant (refractive index, absorption coefficient, or the like) of the non-infiltrative member for the THz wave used is approximately equal to that of the infiltrative holding member, and there is a case where this is not so. The former case is a case where the detection is performed under a condition wherein THz wave propagating along the transmission path is not strongly reflected at a boundary between the infiltrative holding member and the non-infiltrative member. The latter case is a case where the reflection at the boundary between the infiltrative holding member and the non-infiltrative member is positively used, and a THz-wave resonator or THz-wave filter is constructed. In this latter case, the detection of the liquid sample is performed based on a change in properties of the THz-wave resonator or THz-wave filter caused by the supply of the liquid sample to the infiltrative holding member.

When a metal microstrip line is used as the transmission path, the infiltrative holding member is disposed crossing its signal line, for example. In another case, the infiltrative holding member can be used as the dielectric between the signal line and the ground plane of the transmission path. It is preferable that the infiltrative holding member is disposed exclusively in the transmission path, or a nearby region where the electric field of the THz wave is relatively strongly distributed. Thereby, an effective interaction between the liquid sample and the THz wave can be achieved, and precision of the detection can be improved.

Figure 9A:
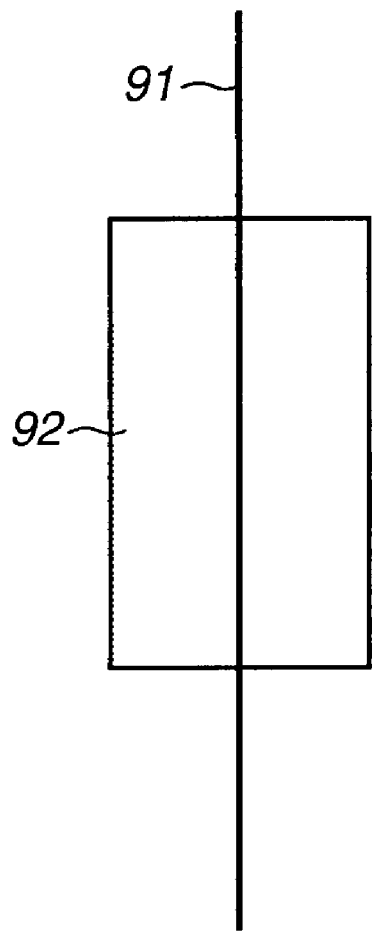
FIG. 9A is a plan view illustrating a location of an infiltrative holding member (a porous material) relative to a transmission path.
Figure 9C:
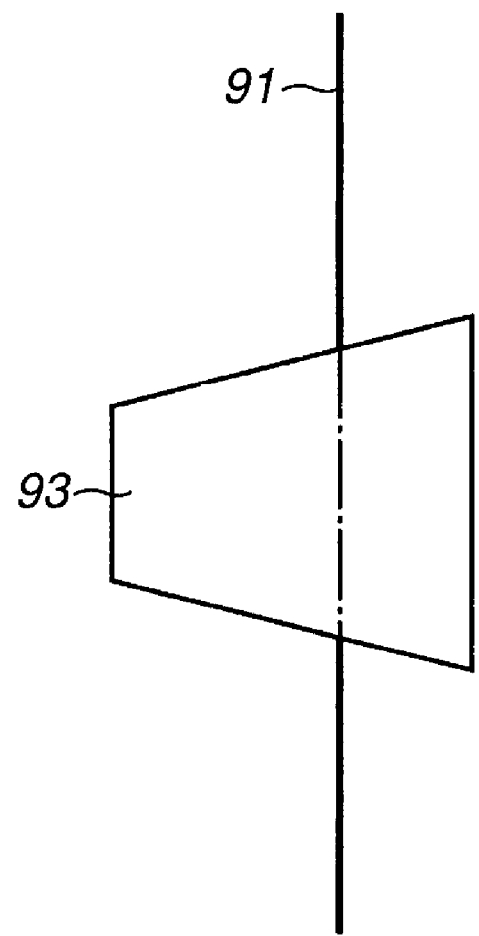
FIG. 9C is another plan view illustrating a location of an infiltrative holding member (a porous material) relative to a transmission path.
Figure 9B:
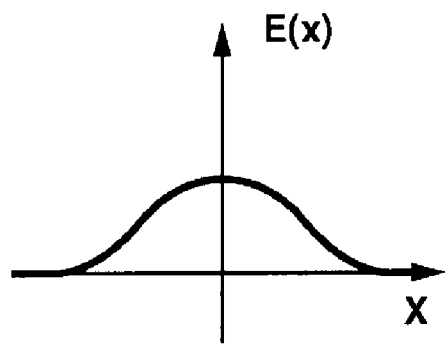
FIG. 9B is a graph showing an electric field distribution of THz wave propagating along the transmission path in FIG. 9A.
Figure 9D:
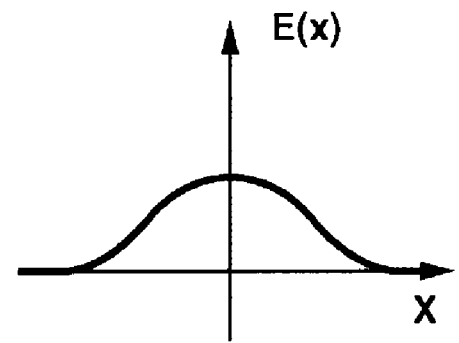
FIG. 9D is a graph showing an electric field distribution of THz wave propagating along the transmission path in FIG. 9C.

For example, when the infiltrative holding member 92, such as a porous material, is disposed on a plane parallel with a substrate including the signal line 91 (the transmission path), as illustrated in FIG. 9A, the electric field present on this plane is distributed symmetrically about a geometrically symmetric center line of the signal line, as shown in FIG. 9B. In such a case, the interaction between the sample in the infiltrative holding member and the THz wave propagating along the transmission path becomes strongest when the geometrically symmetric center line of the electric field is approximately aligned with the geometrically symmetric center line of the signal line. Where $E(0)=1$ is set in FIG. 9B, the interaction between the wave and the object can virtually occur down to a location of $E(x)=1/e^2$. Therefore, the infiltrative holding member should be set in a range of $E(x)>1/e^2$. Needless to say, it is best to set the object at a location of $E(0)=1$. FIG. 9D, FIG. 10B and FIG. 10D also show electrical field distributions, respectively. The infiltrative holding members have various shapes, and the curve of the electrical field distribution varies depending on the shape of the infiltrative holding member.

Further, also when the infiltrative holding member is used as the dielectric between the signal line and the ground plane, the electric field present on a plane parallel with the substrate and near the ground plane is distributed symmetrically about a geometrically symmetric center line parallel with the signal line. Accordingly, also in this case, the interaction between the sample in the infiltrative holding member and the THz wave propagating along the transmission path becomes strongest when the symmetrical center line of the electric field is approximately aligned with the symmetrical center line of the signal line.

There is a case where two symmetrical center lines of the electric field distribution extending in directions parallel and perpendicular to the propagation direction of the THz wave exist. In such a case, it is preferable that the symmetrical center line of the electric field distribution parallel with the propagation direction is approximately aligned with the symmetrical center line of the infiltrative holding member.

In general, observing in a plane parallel with the substrate constituting the transmission path, the electric field distribution of the THz wave along the transmission path is symmetrical about a center line parallel with the symmetrical center line of the transmission path. In such a case, the interaction between the sample in the infiltrative holding member and the THz wave propagating along the transmission path becomes strongest when the symmetrical center line of the electric field distribution in a plane wherein the infiltrative holding member is set is approximately aligned with the center line of the infiltrative holding member.

Further, for example, when the infiltrative holding member 93, such as a porous material, is asymmetrical as illustrated in FIG. 9C, it is preferable that a geometrical gravity center line (a line passing a center of gravity) of the infiltrative holding member is approximately aligned with the symmetrical center line of the electric field distribution shown in FIG. 9D.

Figure 10A:
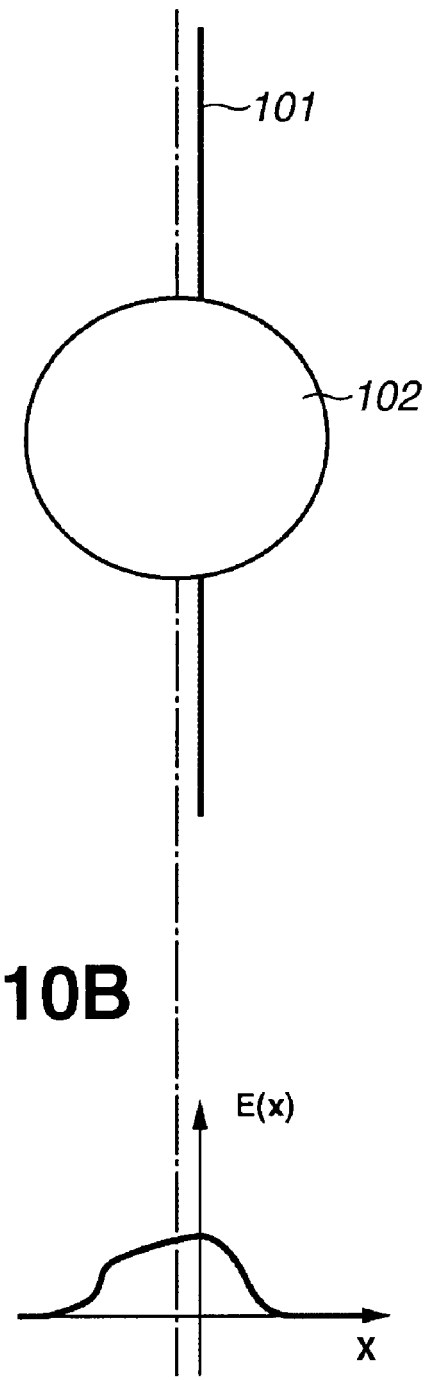
FIG. 10A is another plan view illustrating a location of an infiltrative holding member (a porous material) relative to a transmission path.
Figure 10C:
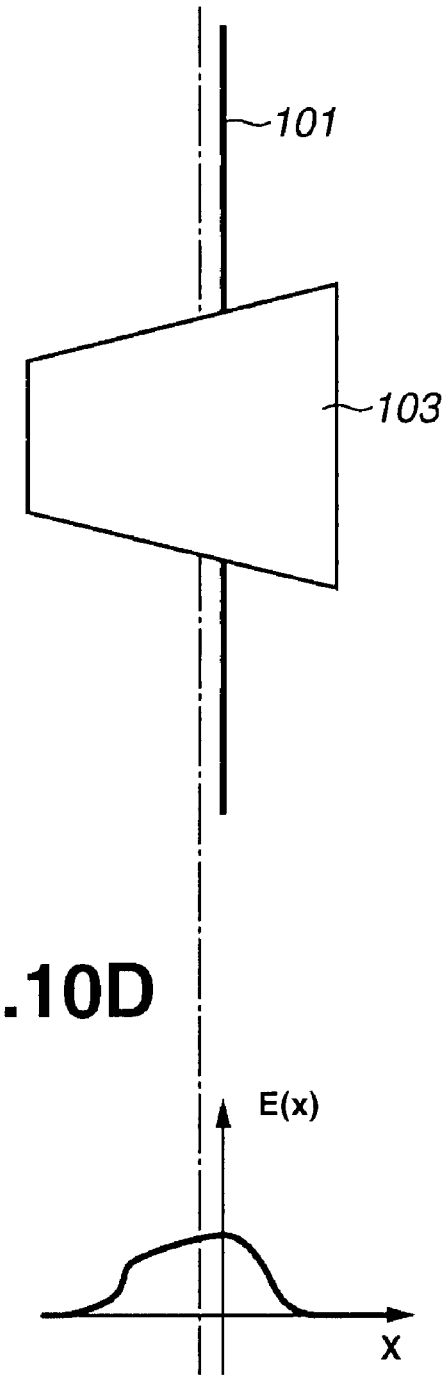
FIG. 10C is another plan view illustrating a location of an infiltrative holding member (a porous material) relative to a transmission path.
Figure 10B:
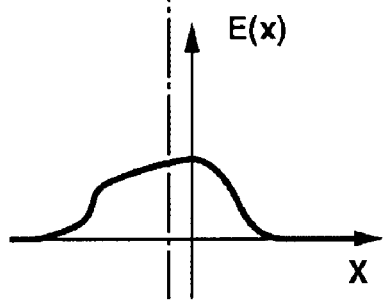
FIG. 10B is a graph showing an electric field distribution of THz wave propagating along the transmission path in FIG. 10A.
Figure 10D:
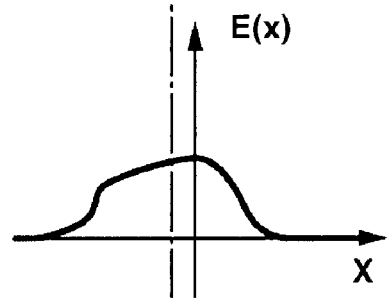
FIG. 10D is a graph showing an electric field distribution of THz wave propagating along the transmission path in FIG. 10C.

Furthermore, for example, when the electric field distribution of the THz wave is asymmetrical as illustrated in FIGS. 10A to 10D, it is preferable that a geometrical gravity center line of the electric field distribution is approximately aligned with the symmetrical center line (in the case of FIGS. 10A and 10B), or the geometrical gravity center line (in the case of FIGS. 10C and 10D) of the infiltrative holding members 102 and 103, respectively. In FIGS. 10A and 10C, element 101 depicts the signal line.

Changes in transmission condition of the THz wave due to the sample infiltrated in the infiltrative holding member include a change in strength of the THz wave, a change in electric field amplitude or waveform of the THz wave, and the like. When a time domain waveform of the THz wave is obtained, a spectrum of the THz wave transmitted through the transmission path can be acquired by Fourier-transforming the time domain waveform. The detection of the sample can be achieved based on the change in the spectrum. Refractive index, transmissivity, absorption coefficient, or the like can be obtained from those changes. Thus, information of the sample, such as its identification, can be obtained.

The infiltrative holding member preferably has a high and uniform transmissivity over the overall frequency of the THz wave propagating the transmission path. Since the frequency range of the THz wave propagating the transmission path depends on properties of a THz-wave generating source and the structure of the transmission path, actually required characteristics of a high and uniform transmissivity vary depending on cases.

A manner of arrangement of the infiltrative holding member on the transmission path varies depending on whether the structure (a structure determining the effective dielectric constant, and the like) of the infiltrative holding member is isotropic or anisotropic for the THz wave propagating the transmission path. Further, the manner of arrangement of the infiltrative holding member on the transmission path varies depending on whether the liquid sample infiltrates in the infiltrative holding member in an isotropic or anisotropic fashion. More specifically, when the infiltrative holding member is isotropic, the infiltrative holding member can be set on the transmission path without considering its arrangement direction, and accordingly it can be arranged easily. When the infiltrative holding member is anisotropic, the infiltrative holding member needs to be set on the transmission path, for example, with the characteristic direction of the infiltrative holding member being aligned with the extending direction of the transmission path, or a direction perpendicular thereto. Thereby, reproducibility of the detection of the liquid sample can be improved.

As a material that has a high and uniform transmissivity as stated above, there are porous materials with a granular or sponge structure formed of polypropylene, polysulfone, nylon, and polyethersulfone. These examples are also isotropic infiltrative holding members. The porous material with a granular structure is a material in which a large number of fine particles disperse and are in contact with each other at point or surface. The porous material with a sponge structure is a material in which a large number of fine porosities disperse in a background material. A porous material with a granular structure, in which a large number of fine particles disperse in an isotropic fashion (i.e., the charging rate of fine particles is substantially constant in every unit region), and which includes substantially no fibrous structure, is a preferable isotropic infiltrative holding member. Further, a porous material with a sponge structure, in which a large number of fine porosities disperse in an isotropic fashion (i.e., the volumetric rate of fine porosities is substantially constant in every unit region), and which includes substantially no fibrous structure, is a preferable isotropic infiltrative holding member.

Inventors of the present invention performed the following experiment to obtain transmissivities of various porous materials. In this experiment, the detection was conducted by a so-called terahertz time-domain spectroscopy in which THz-wave pulses are generated from a photoconductive antenna, the THz-wave pulses are transmitted in a space, and the THz-wave pulses are detected by another photoconductive antenna. A sheet porous material is arranged in a transmission path of the THz-wave pulses, to obtain the transmissivity of the porous material.

According to results of the above experiment, it can be understood that every porous material exhibits a preferable transmissivity. Particularly, the porous materials with a granular or sponge structure formed of polypropylene, polysulfone, nylon, and polyethersulfone exhibits the following result. The transmissivity for THz wave at 2.0 THz is above 90 percent, and a value v' defined by the following formula (1) showing a uniformity of the transmissivity is above 20 (see the following Tables 1-1 and 1-2). Here, the transmissivity is an amplitude transmittance defined by a ratio of an absolute value of amplitude of THz wave after transmission through the porous material relative to that before transmission through the porous material.

$$v' = |T_M - 1|/|T_L - T_H| \tag{1}$$

v' is equal to a value obtained by dividing a value (which is obtained by subtracting 1 (one) from a transmissivity $T_M$ at a frequency near a center between uppermost frequency and lowermost frequency of THz wave used for measurement) by a difference between a transmissivity $T_H$ at the uppermost frequency and a transmissivity $T_L$ at the lowermost frequency, and taking an absolute value of this quotient. This value exhibits a degree of uniformity of the transmissivity over a frequency range. As the value v' increases, the frequency dependency of the transmissivity decreases. For example, at an extreme where the value v' is infinite, the value v' is independent of the frequency. The indication of uniformity of the transmissivity by the formula (I) is defined with reference to Abbe's number used in the field of optical material for showing the frequency dependency of a refractive index. Hereinafter, the value P' will be referred to as a transmissivity Abbe's number.

TABLE 1-1

| main material of membrane filter | amplitude transmissivity | | | porosity | | |
|---|---|---|---|---|---|---|
| | 0.5 THz | 1.0 THz | 2.0 THz | diameter (micron) | thickness (micron) | use |
| polypropylene | 100 | 98 | 96 | 0.45 | 114 | solution and solvent usable |
| Polysulfone | 97 | 97 | 100 | 0.45 | 145 | sterilization and filtration of living object and medicine |

TABLE 1-1-continued

| main material of membrane filter | amplitude transmissivity | | | porosity | | use |
| --- | --- | --- | --- | --- | --- | --- |
| | 0.5 THz | 1.0 THz | 2.0 THz | diameter (micron) | thickness (micron) | |
| polyethersulfone | 98 | 96 | 100 | 0.45 | 140 | sterilization and filtration of living object and medicine |
| Nylon | 97 | 96 | 95 | 0.45 | 127 | suitable for organic solvent |
| polyvinyliden-difluoride | 98 | 96 | 84 | 0.45 | 147 | suitable for protein and nucleic acid |
| nitro cellulose | 97 | 91 | 85 | 0.2 | 145 | western transfer |
| Cellulose | 95 | 89 | 70 | 20 to 25 | 210 | for analysis of Al, etc. |
| glass fiber | 98 | 90 | 80 | 1.6 | 260 | monitoring of atmospheric pollution |
| cellulose-mixed-ester | 98 | 95 | 88 | 0.8 | 152 | Micro-bioassay |
| quartz fiber | 98 | 99 | 82 | | 450 | atomic absorption analysis and emission spectroscopy |

TABLE 1-2

| main material of membrane filter | property | filtration rate | uniformity (eccentricity) *1 | Abbe's number | porosity property |
| --- | --- | --- | --- | --- | --- |
| polypropylene | adsorption of low protein | high | 1.02 | 24.3 | sponge-like |
| polysulfone | adsorption of low protein | high | 1.09 | 32.0 | sponge-like |
| polyether-sulfone | adsorption of low biomolecule | high | 1.00 | 47.5 | granular |
| nylon | hydrophilicity of membrane itself | high | 1.01 | 47.5 | sponge-like |
| polyvinyliden-difluoride | resistivity to biosolvent | no filtration | incapable of estimation | 6.79 | fibrous and granular |
| nitro cellulose | high coupling ability to protein and nucleic acid | very low | 1.16 | 7.50 | fibrous |
| cellulose | for gelatin-like precipitant | very high | 1.11 | 3.52 | fibrous |
| glass fiber | high filtration rate and holding of fine particles | very high | not clear | 4.94 | fibrous |
| cellulose-mixed-ester | high capture rate | low | 1.36 | 9.40 | fibrous and sponge-like |
| quartz fiber | low background | very high | 1.12 | 6.13 | fibrous |

Note:
In the column of *1, 1.0 represents a true circle, polyvinyliden-difluoride is incapable of estimation since liquid cannot infiltrate in polyvinyliden-difluoride, and glass fiber is not clear since the boundary of liquid infiltration area is not clear.

The above granular or sponge structure can be distinguished from a non-granular or non-sponge structure by the following criteria. Where a liquid droplet is dripped on a sheet porous material, the sheet porous material can be deemed to have a granular or sponge structure when a spread of the dripped droplet is approximately circular. The sheet porous material cannot be deemed to have a granular or sponge structure when a spread of the dripped droplet is non-circular, such as elliptical. In the case of a non-circular spread, the spread can be determined to be non-uniform when a value obtained by dividing a longer diameter by a shorter diameter of the ellipse or the like is over 1.11. Therefore, with respect to boundary structures between the granular or sponge structure and the non-granular or non-sponge structure, the porous material can be deemed to have a granular or sponge structure if the spread shows the above value of less than 1.11.

To paraphrase the above, the porous materials with a granular or sponge structure formed of polypropylene, polysulfone, nylon, and polyethersulfone have a relatively wide range over which the transmissivity is high for THz wave, and can be used as a preferable infiltrative holding material.

A porous material with a granular or sponge structure formed of material having a high transmissivity for THz wave is also preferable even if the material is other than the above-stated polypropylene, polysulfone, nylon, and polyethersulfone. Such a porous material is considered to have a relatively high transmissivity, and a large uniformity of the transmissivity for THz wave.

The principal object of the infiltrative holding member is to hold the liquid sample or object. Therefore, the infiltrative holding member is not necessarily a porous material with a granular or sponge structure formed of the above-stated polypropylene, polysulfone, nylon, or polyethersulfone. Further, the actual frequency range of generated or detected THz wave can be without a range between 0.5 THz and 2.0 THz described in the Tables 1-1 and 1-2 because of the structure of the transmission path and properties of the THz-wave generator. Accordingly, it is permissible to use a material having a sufficiently high and uniform transmissivity for THz wave in an actual frequency range.

The above-discussed porous material with a granular or sponge structure has an isotropic structure, so that it can be advantageously set on the transmission path without considering its arrangement direction. In contrast, the porous material with a fibrous structure can improve reproducibility of the detection when it is set on the transmission path, for example, with its fibrous direction being aligned with the extending direction of the transmission path, or a direction perpendicular thereto. Further, when the liquid sample is dripped on the porous material with a fibrous structure, the sample is likely to infiltrate in an elliptical form. Therefore, when a longer-diameter direction of the ellipse is aligned with the extending direction of the transmission path, it is possible to achieve an effective interaction between THz wave and the liquid sample, and improve sensitivity of the detection.

The embodiments will be described in more detail with reference to FIGS. 1A to 1C. In the detecting apparatus of the first embodiment, a ground of the transmission path is a metal plane 12 formed on a substrate 11 by vacuum evaporation or the like. The substrate 11 is, for example, a silicon substrate. The metal plane 12 is made of, for example, 500 Å thin titanium and 3000 Å thin gold. On the metal plane 12, two LT (low-temperature)-GaAs layers 13a and 13b are formed by epitaxial lift-off or the like. A dielectric layer 14 relatively transparent for THz wave is formed on the LT-GaAs layers 13a and 13b. The dielectric layer 14 is made of, for example, BCB (benzocyclobutene). The thickness of the dielectric layer 14 is 5 microns, for example. A portion of the dielectric layer 14 is removed, and the LT-GaAs layers 13a and 13b are partly exposed. On the dielectric layer 14, a metal line (a signal line) 15 is formed extending with a width of about 5 microns to 10 microns, and a longitudinal length of about 1 mm. Gaps 16a and 16b of about 5 microns to 10 microns are formed in two areas along the metal line 15. Electrodes 18a, 18b, 18c, and 18d are provided at end portions of the metal line 15. A transmission path 101 is constructed to extend in the extending direction of the metal line 15.

A porous material 17 is disposed on the metal line 15. The porous material 17 is an infiltrative holding member for holding a liquid sample by capillary force and the like. For example, a rectangular membrane filter is used as the porous material 17. The porous material 17 is set by bonding adhesive whose loss for THz wave is small, or by pressing it against the transmission path 101 with another member. A method of pushing the porous material 17 against the transmission path 101 with a resin plate (non-infiltrative member) 19 will be described.

In this method, a hole is formed in the polystyrene plate 19 having a thickness of about 1 mm, and the porous material 17 with an outer size slightly larger than the hole is set covering the hole therewith, using bonding adhesive or the like. The polystyrene plate 19 is disposed such that the porous material 17 crosses the metal line 15 at a location between the two LT-GaAs layers 13a and 13b. Preferably, the symmetrical center line of the porous material 17 is approximately aligned with the line 15. The reason therefor is as follows. With the transmission path 101 of the microstrip line type as described above, the electric field of THz wave becomes stronger at a location as the location approaches the center of the metal line 15. Accordingly, interaction between the liquid sample held in the porous material 17 and THz wave propagating along the transmission path 101 becomes stronger when the symmetrical center line of the porous material 17 is approximately aligned with the line 15. Further, it is preferable to bring the porous material 17 into contact with the line 15 since the above interaction increases.

A marker (alignment mark) 100 can be provided at a portion of the porous material 17 or polystyrene plate 19, and a portion of the dielectric layer 14 for the purpose of achieving such an accurate arrangement that the symmetrical center line of the porous material 17 is approximately aligned with the line 15.

The refractive index of the polystyrene plate 19 for THz wave is preferably close to that of the porous material 17. This is because if those refractive indices are largely different, reflection and the like due to impedance mismatch may occur at the boundary. For example, a membrane filter (a product by Nihon Pall Ltd.; product No. 60172) formed of hydrophilic polyethersulfone with an average porosity diameter of 0.45 micron can be used as the porous material 17, and a polystyrene plate coated with hydrophobic foamy styrene can be used as the polystyrene plate 19. In this case, the refractive index of the porous material 17 is about 1.2, and the refractive index of the polystyrene plate 19 is from about 1.05 to about 1.1.

Preferably, the width of the rectangular porous material 17 is approximately over three times as large as the width of the line 15. The transmission path 101 for transmitting THz wave therethrough is composed of the metal plane 12, the dielectric layer 14 and the line 15. With this transmission path of the microstrip line type, the electric field of propagating THz wave is strongly present within a region having a width that is about three times as large as the width of the line 15. Therefore, when the width of the porous material 17 is approximately set over three times as large as the width of the line 15, the interaction between the sample held in the porous material 17 and the propagating THz wave increases. The width of the porous material 17, however, can be made much larger in the light of fabrication convenience. As for the longitudinal length of its side, it is preferably below the length of the transmission path. In this embodiment, length, width, and thickness of the porous material 17 are, for example, about 0.6 mm, about 0.4 mm, and about 150 microns, respectively.

The average porosity diameter of the porous material 17 is, for example, 0.5 micron. Further, the porous material 17 is formed of a material with a high transmissivity for THz wave (e.g., hydrophilic polyethersulfone).

Two electrodes 18a and 18c; 18b and 18d are provided at end portions of the line 15, respectively. A voltage of about 10 V is applied through the electrode 18a in the THz-wave supplying unit, and the electrode 18b in the THz-wave detecting unit is connected to a signal amplifier 110. The other electrodes 18c and 18d are connected to the ground. In this embodiment, the end portions of the line 15 act as a coupler for coupling the THz wave from the supplying unit to the transmission path, and a coupler for coupling the THz wave from the transmission path to the detecting unit, respectively.

In this embodiment, the gap 16a of the THz-wave supplying unit is illuminated with femtosecond (fsec) laser light to generate THz wave, and the THz wave is transmitted toward the gap 16b of the THz-wave detecting unit through the line 15. On the way of transmission through the transmission path, the THz wave interacts with the sample infiltrated in the porous member 17. On the other hand, the gap 16b of the THz-wave detecting unit is illuminated with the fsec laser, and the THz wave transmitted through the line 15 is detected through the signal amplifier 110.

The liquid sample, such as DNA solution, is dripped and infiltrated in the porous member 17 using a micro-injector or the like. The liquid sample is infiltrated and held in the porous member 17 by capillary force and the like. The transmission condition of the THz wave detected by the detecting unit is changed (e.g., attenuated) by the sample held in the porous member 17. Information of the sample can be thus acquired from the spectrum or the like based on the above change.

FIG. 2 illustrates a peripheral optical system which is preferably used by the above detecting apparatus. As illustrated in FIG. 2, fsec pulse laser light emitted from a mode-locked Ti:sapphire laser (fsec laser) 21 is split by a beam splitter 26. One laser light is condensed and illuminated on the gap 16a of the THz-wave supplying unit illustrated in FIG. 1, to which the voltage is applied. The other laser light is transmitted through a time delay optical system 22 by using mirrors 27, and then condensed and illuminated on the gap 16b of the THz-wave detecting unit of FIG. 1, which is connected to the signal amplifier 110.

The interval between gaps 16a and 16b in the detecting apparatus 24 is exceedingly narrow (e.g., about 1 nm). Accordingly, it is preferable to re-collect the split laser light pulses prior to the above condensation and illumination, and project the re-collected light pulses on the gaps through a single object lens 23 or the like, respectively. The time-domain waveform of the THz wave transmitted through the transmission path 101 can be obtained when the time delay system 22 is moved back and forth. Fourier transformation of the obtained time-domain waveform brings forth the spectrum of THz wave whose transmission condition is changed according to characteristics, presence or absence, or the like of the sample. Information of the sample can be thus acquired.

In the above discussion, the porous material is used as the infiltrative holding member, but the fibrous material and the needle-like material can also be used. Further, the porous material 17 is set on the transmission path using the polystyrene plate (non-infiltrative member) 19 in the above description. The infiltrative holding member, however, can be set directly on the transmission path by bonding adhesive, or thermal pressure bonding. Furthermore, the dielectric of the transmission path can be made of a material, such as a porous material, capable of infiltration and holding of the liquid sample by capillary force and the like.

With respect to the structure and configuration of the transmission path, it is not limited to the above microstrip line. The transmission path can also be formed by strip line, coplanar strip line, coplanar waveguide, micro-coplanar strip line, slab line, slot line, or the like.

In the above detecting apparatus and method, the infiltrative holding member for infiltration and holding of the liquid sample is used. Therefore, the location of the liquid sample relative to the transmission path can be regulated accurately. Hence, even the quantitative detection, inspection and measurement of the sample, such as measurement of its concentration, can be precisely achieved in an improved reproducibility. Further, when the liquid sample is dripped and dried in the infiltrative holding member, the thickness of precipitated sample becomes uniform. The spread of the liquid sample in the infiltrative holding member remains unchanged each time the sample is dripped, and hence the volume of interaction between the sample and THz wave does not fluctuate.

In conventional apparatuses and methods, there is a possibility that the sample drop falls, and the interaction volume between the sample and THz wave changes when the transmission path is violently handled prior to sufficient drying of the sample, for example. In the above embodiment, such possibility can be eliminated.

Thus, in the above embodiment, the desired amount of the liquid sample can be accurately set on the transmission path, or near a desired portion thereof, in each detection. Even the quantitative measurement can be readily carried out in a good reproducibility. For example, a living object, such as DNA, can be held in the infiltrative holding member with its three-dimensional configuration being unchanged even when the liquid sample is dried. Precise information of the sample can be acquired.

Description will be made for more specific embodiments and examples. A first embodiment will be described with reference to FIGS. 1A to 1C. The first embodiment corresponds to the above-discussed embodiment. In this embodiment, the porous material 17 attached to the polystyrene plate 19 is prepared, and set on the line 15. The above-noted membrane filter produced by Nihon Pall Ltd. (product No. 60172) is preferably used as the porous material 17. When the polystyrene plate 19 with the porous material 17 attached thereto is disposed on the line 15, the marker (alignment mark) 100 is preferably used. Accordingly, the porous material 17 can be set on a desired location relative to the line 15.

When the liquid sample is infiltrated into the porous material 17 set on the line 15, DNA solution is dripped on the porous material 17 through a hole in the polystyrene plate 19 using a microinjector (e.g., a programmable microinjector IM-300 produced by NARISHIGE SCIENTIFIC INSTRUMENT LAB.). The concentration of the DNA solution is, for example, 0.5 microgram/microliter. The dripped amount is, for example, 30 nl. The dripped DNA solution is infiltrated and held in the porous material 17, and reaches a contact interface between the signal line 15 and the porous material 17. In the case the dripped amount is extremely little (e.g., 1 pl), there is a possibility that the dripped DNA solution does not infiltrate into the overall porous material 17. This substantially impedes effective accomplishment that the interaction region between the sample and THz wave is accurately regulated. Therefore, there is a need to drip an amount enough to achieve infiltration of the liquid sample in the entirety of the porous material 17. Further, also in the case the DNA solution is not sufficiently infiltrated in the porous material 17 due to too dense concentration, too high viscosity, or the like, the effective accomplishment cannot be obtained. In such a case, therefore, the solution should be appropriately thinned, for example. The concentration of the DNA solution in the porous material 17 can be increased by repetition of dripping and drying of the sample.

The DNA solution dripped on the porous material is dried in room temperature. After that, the THz wave generated by the THz-wave supplying unit is transmitted through the transmission path 101 to detect, for example, the time-domain waveform of the THz wave, according to the method as described in the above embodiment.

Figure 3:
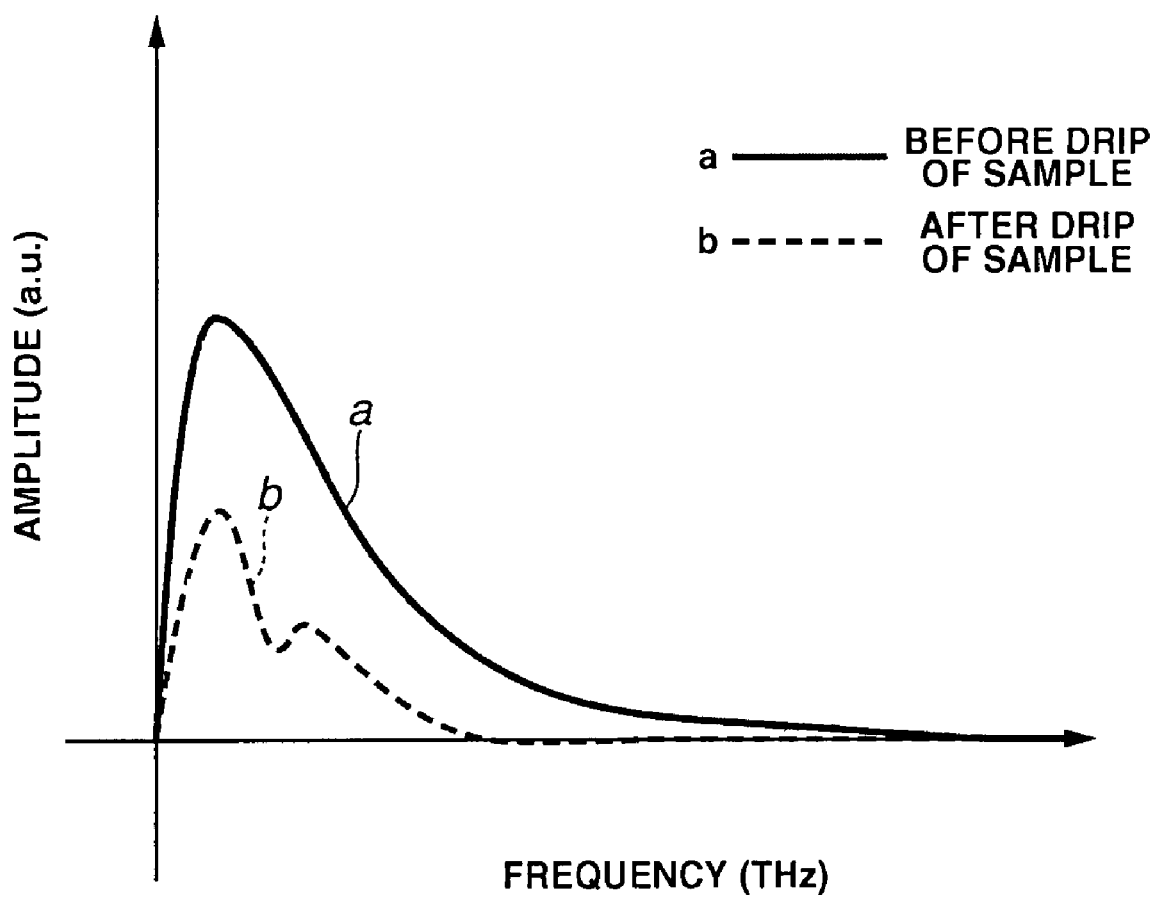
FIG. 3 is a graph showing exemplified spectra of a THz wave detected by a detecting unit of the detecting apparatus of the present invention.

FIG. 3 shows exemplified spectra by Fourier-transforming time-domain waveforms of THz waves transmitted through the transmission path 101 and detected by the THz-wave detecting unit. In FIG. 3, the solid line a illustrates the exemplified spectrum of the THz wave detected before the DNA solution is dripped on the porous material 17, and the dotted line b illustrates the exemplified spectrum of the THz wave detected after the DNA solution is dripped and dried. Information of presence, quantity, and so forth of the DNA can be detected based on the difference of the THz-wave spectra detected before and after the drip of the sample, as illustrated in FIG. 3. In this embodiment, the THz-wave spectrum detected after the drip of the sample can be obtained in a good reproducibility, so that accurate information of the sample can be acquired. In contrast thereto, it is not easy for the conventional technique to stably drip the liquid sample on an appropriate location on the transmission path in a preferable reproducibility. Therefore, according to the conventional technique, the THz-wave spectrum detected after the drip of the sample cannot typically be obtained in a satisfactory reproducibility.

In the first embodiment, the DNA solution is approximately uniformly held in the porous material 17 set on the transmission path 101. Accordingly, reproducibility is obtained in the quantitative measurement, and an accurate quantitative detection is guaranteed. The volume of the porous material 17 is about 0.6 mm (length in a direction parallel with the signal line 15)*0.4 mm (width in a direction perpendicular to the signal line 15)*0.15 mm (thickness). The liquid sample, therefore, can be concentrated in a region over which propagating THz wave is distributed relatively strongly. Thus, efficient and accurate detection can be achieved.

Further, in this embodiment, a frame of the polystyrene plate (non-infiltrative member) 19 exists around the porous material 17. Hence, there is virtually no possibility that the liquid sample comes out of the porous material even if too much liquid sample is dripped beyond liquid holding capability of the porous material 17. When the liquid sample over the volume defined by the polystyrene frame is dripped, excessive liquid sample can be wiped and removed. Thus, the distribution of the liquid sample can be effectively regulated.

Furthermore, the detection can be repetitively performed by removing the used porous material 17 with the resin plate 19 and disposing an unused resin plate with a porous material on the same transmission path 101. When the marker (alignment mark) 100 is provided, the relative positional relation between the line 15 and the porous material 17 can be stably established each time of the detection. The reproducibility can be thus assured.

A second embodiment of the present invention will be described referring to FIGS. 4A to 4C. Also in this embodiment, similar to the first embodiment, the porous material 42 is set crossing the line 41 in the detecting apparatus including the THz-wave supplying unit, the transmission path (microstrip line structure), and the detecting unit. In the second embodiment, two non-infiltrative members or polystyrene plates 43a and 43b are pressed against two sides (parallel with the line 41) of the porous material 42, respectively. The porous material 42 can be thus set. Other structures of the second embodiment are substantially the same as those of the first embodiment. In FIGS. 4A to 4C, reference numerals are omitted with respect to those elements.

The polystyrene plate 43 is preferably slightly larger than the porous material 41 in the longitudinal direction (e.g., 1 mm*0.6 mm). Two polystyrene plates 43a and 43b are preferably spaced from each other by more than thrice the width of the line 41 (i.e., each plate is away from the center of the line 41 by more than 1.5 times the width thereof). The reason is that such arrangement can prevent an impedance change of the transmission path due to the presence of the polystyrene plate 43.

Also in the second embodiment, the gap of the THz-wave supplying unit is illuminated with femtosecond (fsec) laser light to generate THz wave, and the THz wave is transmitted through the transmission path. After interaction with the sample in the porous material 42, the THz wave reaches the THz-wave detecting unit. Thus, the time-domain waveform and forth of the THz wave can be obtained.

In the second embodiment, the porous material 42 is in direct contact with the line 41, and no intervening substance, such as adhesive, exists therebetween. Reliable detection can be expected in this embodiment. Further, the polystyrene plates 43a and 43b extend along the two sides of the porous material 42 as described above. Accordingly, even when much liquid sample beyond the liquid holding capability of the porous material 42 is dripped, virtually no liquid sample spreads toward a direction leaving from the line 41. When the porous material 42 is an anisotropic porous material or fibrous material with properties that liquid therein is hard to spread in a direction parallel with the line 41, the liquid sample remains in the porous material 42. Accordingly, a relatively large liquid sample can be dripped at a time. Thus, the distribution of the liquid sample can be more effectively regulated.

A third embodiment of the present invention will be described referring to FIGS. 5A to 5C. In this embodiment, the porous material 52 is set crossing the line 51 by bonding or the like. For example, adhesive, such as BCB and photoresist, is applied on a peripheral portion of the porous material 52 near its two sides parallel with the line 51, and the porous material 52 is bonded on the transmission path crossing the line 51. The alignment mark can be provided for alignment at the time of bonding. In the third embodiment, the number of elements can be reduced. Other structures of the third embodiment are substantially the same as those of the first embodiment. Also in FIGS. 5A to 5C, reference numerals are omitted with respect to those elements.

Also in the third embodiment, the gap of the THz-wave supplying unit is illuminated with femtosecond (fsec) laser light to generate THz wave, and the THz wave is transmitted through the transmission path. After interaction with the sample in the porous material 52, the THz wave reaches the THz-wave detecting unit. Thus, the time-domain waveform of the THz wave can be obtained, for example.

A fourth embodiment of the present invention will be described referring to FIGS. 6A to 6C. In this embodiment, a hole is formed in the polystyrene plate 63 having a thickness of about 1 mm, and the porous material 62 with an outer size slightly larger than the hole is set covering the hole therewith, using bonding adhesive or the like. The polystyrene plate 63 is the non-infiltrative member of resin having a high transmissivity for THz wave. The size of the hole is about 0.4 mm*0.3 mm, and the size of the porous material 62 is 0.6 mm*0.4 mm, for example. Element 61 represents a metal line (signal line). Other structures of the fourth embodiment are substantially the same as those of the first embodiment. Also in FIGS. 6A to 6C, reference numerals are omitted with respect to those elements.

Figure 6A:
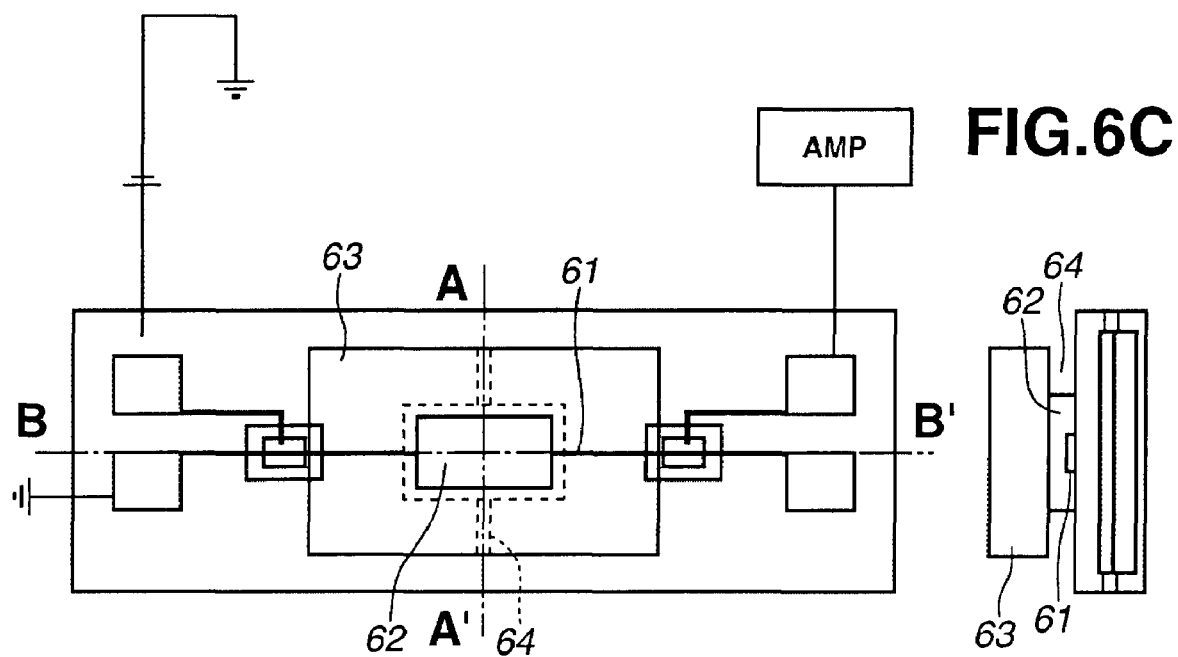
FIG. 6A is a plan view illustrating a fourth embodiment of a detecting apparatus and method according to the present invention, in which a flow path is provided near an infiltrative holding member (a porous material) for infiltration and holding of a liquid sample.
Figure 6C:
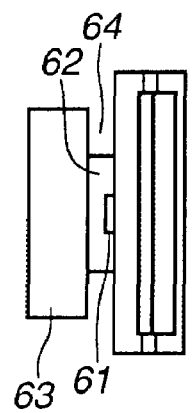
FIG. 6C is a cross-sectional view taken along line A-A' of FIG. 6A.
Figure 6B:
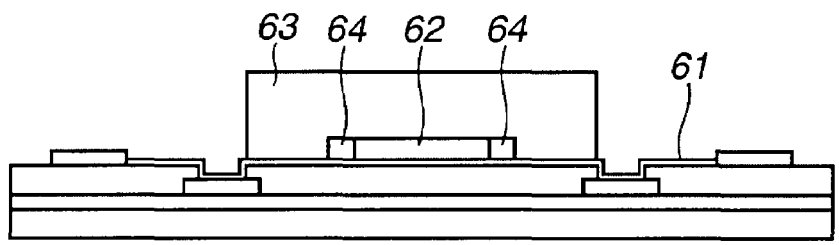
FIG. 6B is a cross-sectional view taken along line B-B' of FIG. 6A.

A flow path 64 can be formed in the polystyrene plate 63 surrounding the porous material 62, as illustrated in FIGS. 6A to 6C. The flow path 64 extends to the side of the polystyrene plate 63. The size of the cross section of the flow path 64 is about 0.05 mm*0.5 mm. In this case, the liquid sample is guided through an inlet port of the flow path 64 in the side of the polystyrene plate 63. The liquid sample dripped in the inlet port of the flow path 64 by the micro-injector or the like reaches the porous material 62 due to capillary force and so forth of the flow path 64. The liquid sample is infiltrated and held in the porous material 62 due to its capillary force and so forth.

The flow path 64 can be connected to a reservoir or the like for storing the liquid sample. In such a structure, the capillary of the micro-injector need not be accurately aligned with the porous material 62 at the time of dripping the liquid sample, so the sample can be readily introduced the porous material 62. Further, the possibility of damaging the porous material or the transmission path with the capillary of the injector can be reduced.

Also in the fourth embodiment, similar to the first embodiment, the THz wave is transmitted through the transmission path. After interaction with the sample in the porous material 62, the THz wave reaches the THz-wave detecting unit. Thus, the time-domain waveform of the THz wave can be obtained, for example.

Figure 7A:
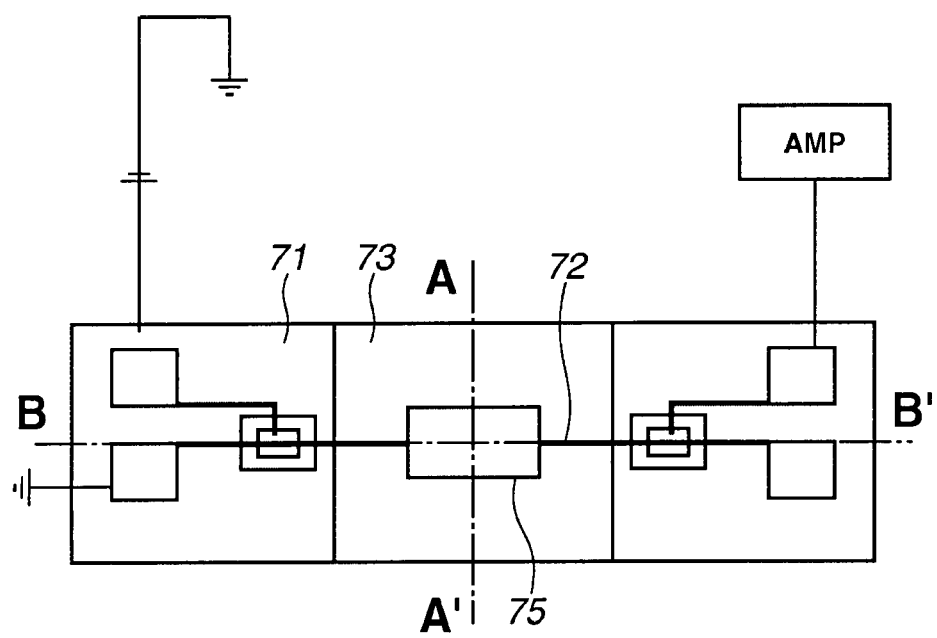
FIG. 7A is a plan view illustrating a fifth embodiment of a detecting apparatus and method according to the present invention, in which a hole is formed in a second resin layer, and an infiltrative holding member (a porous material) for infiltration and holding of a liquid sample is disposed in the hole.
Figure 7C:
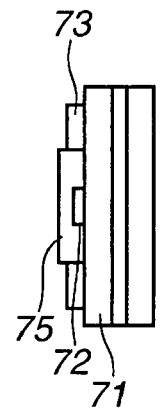
FIG. 7C is a cross-sectional view taken along line A-A' of FIG. 7A.
Figure 7B:
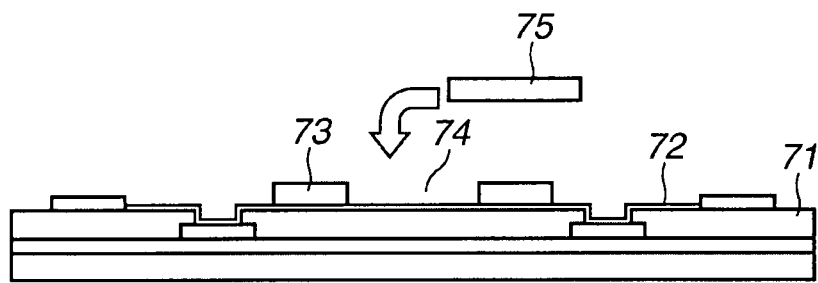
FIG. 7B is a cross-sectional view taken along line B-B' of FIG. 7A.

A fifth embodiment of the present invention will be described referring to FIGS. 7A to 7C. In this embodiment, a second resin layer 73 is formed on a BCB layer 71 in the detecting apparatus including the THz-wave supplying unit, the transmission path (microstrip line structure), and the detecting unit. A hole 73 is formed in a portion of the second resin layer 73 by plasma etching or the like. The second resin layer (non-infiltrative member) 73 is formed of a material (e.g., BCB) that cannot infiltrate and hold the liquid sample therein. The second resin layer 73 can be formed of photoresist, and the hole 74 can be formed by photolithography or the like.

The size of the hole 74 is about the same as or slightly larger than the size of the porous material 75. The porous material 75 is set in the hole 74. A gap can be formed between the porous material 75 and the edge of the hole 74. In another configuration, the porous material 75 can be in contact with the edge of the hole 74. The thickness of the second resin layer 73 can be larger or smaller than the thickness of the porous material 75. The porous material 75 is set in the hole 74 with two sides of the porous material 75 parallel with the line 72 being bonded by adhesive or the like. Other structures of the fifth embodiment are substantially the same as those of the first embodiment. Also in FIG. 7A to 7C, reference numerals are omitted with respect to those elements.

In the fifth embodiment, the non-infiltrative member and the flow path as described in the third and fourth embodiments can be fabricated integrally. Therefore, the number of the elements can be reduced in the fifth embodiment.

A sixth embodiment will be described with reference to FIGS. 8A to 8C. In the detecting apparatus of the sixth embodiment, the ground of the transmission path is a metal plane 82 formed on a substrate 81 by vacuum evaporation or the like. The substrate 81 is, for example, a silicon substrate. The metal plane 82 is made of, for example, 500 Å thin titanium and 3000 Å thin gold. On the metal plane 82, two LT-GaAs layers 83a and 83b are formed by epitaxial lift-off or the like. The dielectric layer 86 transparent for THz wave is formed on the metal plane 82. Windows are then formed in portions on the two LT-GaAs layers 83a and 83b, and a portion therebetween. The porous material 84 is set in the window formed on the two LT-GaAs layers 83a and 83b by thermal pressure bonding, adhesive bonding, or the like. The window in the resin layer 86 is slightly larger than the porous material 84 so that the liquid sample can be supplied through the side of the porous material 84. The porous material 84 is beforehand processed such that its surface opposite to the side of the substrate can be a smooth flat face with porosities thereon being packed. Alternatively, a resin film or the like is attached on the above surface of the porous material 84.

The metal line 85 is formed on the surface of the above structure by vacuum evaporation or the like. The metal plane 82, the porous material 84 and the line 85 constitute the transmission path of the microstrip line type. In this embodiment, the porous material 84 serves as the dielectric layer of the transmission path, too. Other structures of the sixth embodiment are substantially the same as those of the first embodiment. Also in FIGS. 8A to 8C, reference numerals are omitted with respect to those elements.

In the above structure, a glass capillary 86 is placed near the side of the porous material 84 to supply the liquid sample thereby. The liquid sample is thus infiltrated in the porous material 84. The flow path can be used in place of the glass capillary.

In this embodiment, the porous material 84 is provided in the dielectric layer of the transmission path, so that the liquid sample can be supplied to a predetermined location in a strong electric field distribution with a predetermined volume. Also in the sixth embodiment, the THz wave is transmitted through the transmission path. After effective interaction with the sample in the porous material 84, the THz wave reaches the THz-wave detecting unit. Thus, the time-domain waveform of the THz wave can be accurately obtained, for example.

A seventh embodiment will be described. In the detecting apparatus of the seventh embodiment, the liquid sample infiltrated in the porous material is cooled and frozen. When the liquid sample containing volatile liquid is infiltrated in the porous material, the liquid evaporates with time, and only non-volatile constituent remains in the porous material. The result of detection of the liquid sample varies with time since the evaporation proceeds with time. Further, time to be required for the evaporation and moisture content of the sample after the evaporation vary depending on ambient conditions, such as temperature and humidity of a place where the liquid sample exists.

To overcome such problem and acquire a stable result of detection, the liquid sample infiltrated in the porous material is cooled and frozen. Freezing is performed at such a timing that the condition of the sample to be detected cannot vary with time. The freezing can be conducted by a method of blowing cold (e.g., coolant and liquid nitrogen) on the measurement sample to directly freeze the sample, or a method of cooling the transmission path to indirectly freeze the sample using a Peltier device or the like, for example.

At the time of freezing, the porous material, such as the membrane filter, also serves as a heat insulating material for preventing heat from flowing into the frozen sample from outside.

This embodiment can be employed for detection of a material contained in liquid from a living object. For example, sweat or blood is infiltrated and frozen in the porous material, and alcohol, sugar or the like therein is measured. Further, it is possible to infiltrate and freeze, in the porous material, a volatile liquid containing fine particles whose diameter are below the porosity diameter of the porous material, and detect such particles.

As described in the foregoing, according to the present invention, it is possible to provide devices using electromagnetic waves at frequency or frequencies in a range between 30 GHz and 30 THz.

Except as otherwise disclosed herein, the various components shown in outline or in block form in the figures are individually well-known and their internal construction and operation are not critical either to the making or using of the present invention or to a description of the best mode of the invention.

While the present invention has been described with respect to what is presently considered to be the embodiments and examples, it is to be understood that the invention is not limited to the disclosed embodiments and examples. The present invention is intended to cover various modifications and equivalent arrangements included within the spirit and the scope of the appended claims.

This application claims priority from Japanese Patent Application No. 2006-108563, filed Apr. 11, 2006, and Japanese Patent Application No. 2007-023610, filed Feb. 2, 2007, the contents of which are hereby incorporated by reference.

What is claimed is:

1. A detecting apparatus for detecting information of a liquid object, the detecting apparatus comprising:
    a transmission path;
    an electromagnetic-wave supplying unit for supplying an electromagnetic wave in a frequency range between 30 GHz and 30 THz to the transmission path;
    an electromagnetic-wave detecting unit for detecting the electromagnetic wave transmitted through the transmission path; and
    an infiltrative holding member for infiltration and holding of the liquid object,
    wherein the infiltrative holding member is set at a location containing at least a portion in which an electric field distribution of the electromagnetic wave propagating along the transmission path extends,
    wherein a non-infiltrative member which is incapable of infiltrating the liquid object is set partly or entirely surrounding the infiltrative holding member,
    wherein a spacing, whose size is less than a wavelength of the electromagnetic wave supplied by the electromagnetic-wave supplying unit, is present between the infiltrative holding member and the non-infiltrative member, and
    wherein the spacing between the infiltrative holding member and the non-infiltrative member comprises a flow path for supplying the liquid object to the infiltrative holding member.

2. The detecting apparatus according to claim 1, wherein the transmission path comprises a metal.

3. The detecting apparatus according to claim 1, wherein a geometrically symmetric center line, or a geometrical gravity center line of the infiltrative holding member is aligned with a geometrically symmetric center line, or a geometrical gravity center line parallel with a propagation direction of the electric field distribution of the electromagnetic wave propagating along the transmission path.

4. The detecting apparatus according to claim 1, further comprising a marker for setting the infiltrative holding member relative to the transmission path.

5. The detecting apparatus according to claim 1, wherein the infiltrative holding member comprises one of a porous material, a fibrous material, and a needle structure.

6. The detecting apparatus according to claim 1, wherein the non-infiltrative member is set partly or entirely surrounding the infiltrative holding member at a position perpendicular to the electromagnetic wave transmitted through the transmission path and at a position where the liquid object is infiltrated.

7. The detecting apparatus according to claim 1, wherein the infiltrative holding member is a granular structure or a sponge structure in which the liquid object infiltrates into the infiltrative holding member isotropically, and the infiltrative holding member is disposed such that the electromagnetic wave transmitted through the transmission path and the liquid object interact with each other.

* * * * *